US008793199B2

(12) United States Patent
Syeda-Mahmood et al.

(10) Patent No.: US 8,793,199 B2
(45) Date of Patent: Jul. 29, 2014

(54) EXTRACTION OF INFORMATION FROM CLINICAL REPORTS

(75) Inventors: Tanveer F Syeda-Mahmood, Cupertino, CA (US); Laura Chiticariu, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 322 days.

(21) Appl. No.: 13/408,906

(22) Filed: Feb. 29, 2012

(65) Prior Publication Data

US 2013/0226841 A1 Aug. 29, 2013

(51) Int. Cl.
*G06F 15/18* (2006.01)

(52) U.S. Cl.
USPC .......................................................... 706/12

(58) Field of Classification Search
None
See application file for complete search history.

(56) References Cited

U.S. PATENT DOCUMENTS

| | | | |
|---|---|---|---|
| 5,537,586 A | 7/1996 | Amram et al. | |
| 5,664,109 A | 9/1997 | Johnson et al. | |
| 5,784,635 A | 7/1998 | McCallum | |
| 5,809,476 A | 9/1998 | Ryan | |
| 6,055,494 A | 4/2000 | Friedman | |
| 6,182,029 B1 | 1/2001 | Friedman | |
| 6,438,533 B1 | 8/2002 | Spackman et al. | |
| 6,556,964 B2 | 4/2003 | Haug et al. | |
| 6,694,307 B2 | 2/2004 | Julien | |
| 6,915,254 B1 | 7/2005 | Heinze et al. | |
| 7,512,576 B1 * | 3/2009 | Syeda-Mahmood et al. | 706/45 |
| 7,610,192 B1 | 10/2009 | Jamieson | |
| 7,624,029 B1 | 11/2009 | Ghouri | |
| 7,783,342 B2 * | 8/2010 | Syeda-Mahmood et al. | 600/523 |
| 7,792,783 B2 | 9/2010 | Friedlander et al. | |
| 7,836,356 B2 * | 11/2010 | Haas et al. | 714/47.1 |
| 8,417,709 B2 * | 4/2013 | Chiticariu et al. | 707/743 |
| 2002/0198739 A1 | 12/2002 | Lau et al. | |
| 2004/0220831 A1 | 11/2004 | Fabricant | |
| 2005/0240439 A1 | 10/2005 | Covit et al. | |
| 2010/0036680 A1 | 2/2010 | Familant | |

OTHER PUBLICATIONS

Covit "Robert Wood Johnson University Hospital deploys EMscribe Dx computer assisted coding solution", Life Science Weekly, Mar. 14, 2006, p. 1039, 2 pages.
EMscribe, A Comprehensive Enterprise Coding Solution. Retrieved from http://www.artificialmed.com/Coding.htm, Copyright 2004-2010 artificial medical intelligence, 2 pages. Last accessed Jun. 10, 2011.
Popescu "An Ontological Fuzzy Smith-Waterman with Applications to Patient Retrieval in Electronic Medical Records" FUZZ-IEEE, (Sep. 2010), 6 pages.

(Continued)

*Primary Examiner* — Michael B Holmes
(74) *Attorney, Agent, or Firm* — Jeffrey T. Holman (57) ABSTRACT

A phrase matching system is described. The system includes a training engine and a matching engine. The training engine is configured to: learn terms and term variants from a training corpus, wherein the terms and the term variants correspond to a specialized dictionary related to the training corpus; and generate a list of negative indicators found in the training corpus. The matching engine is configured to: perform a partial match of the terms and the term variants in a set of electronic documents to create initial match results; and perform a negation test using the negative indicators and a positive terms test using the terms and the term variants on the initial match results to remove matches from the initial match results that fail either the negation test or the positive terms test, resulting in final match results.

13 Claims, 4 Drawing Sheets

(56) References Cited

OTHER PUBLICATIONS

Zhou et al. "Converting Semi-structured Clinical Medical Records into Information and Knowledge", Proceedings of the 21st International Conference on Data Engineering (2005), 8 pages.
Uchida et al. "Extraction of Important Keywords in Free Text of Questionnaire Data and Visualization of relationship among sentences", FUZZ-IEEE, Korea (Aug. 2009), p. 1604-1608.
Claster et al. Text Mining in Radiological Data Records: an Unsupervised Neural Network Approach, Proceedings of the First Asia International Conference on Modeling & Simulation (2007), 5 pages.
Bhagwan et al."Large-scale text mining for disease mentions" submitted to ACM Conference on Healthcare Informatics, 2010.
Xu et al. "Medex: a medication information extraction system for clinical narratives", American Medical Informatics Association, vol. 7, Issue 1, (Jan./Feb. 2010), pp. 19-24.
Reiss et al. "An algebraic approach to rule-based information extraction", IEEE International Conference on Data Engineering, (2008), 10 pages.
Iavindrasana et al. "Clinical data mining: a review", IMIA Yearbook of Medical Informatics, (2009), pp. 121-133.
Tange et al. "Medical narratives in electronic medical records", International Journal of Medical Informatics, vol. 46, Issue 1, (Aug. 1997), Abstract, 1 page.
Meystre et al."Extracting information from textual documents in the electronic health record: a review of recent research" IMIA Yearbook of Medical Informatics, (2008), pp. 128-144.
Cohen et al."A survey of current work in biomedical text mining" Briefings in Bioinformatics, vol. 6, Issue 1, (Mar. 2005), pp. 57-71.
Spasic et al."Text mining and ontologies in biomedicine: making sense of raw text" Briefings in Bioinformatics, vol. 6, Issue 3, (Sep. 2005), pp. 239-251.
Turchin et al. "Comparative evaluation of accuracy of extraction of medication information from narrative physician notes by commercial and academic natural language processing software packages" AMIA Annual Symposium Proceedings, (2006), pp. 789-793.
Zeng et al "Extracting principal diagnosis, co-morbidity and smoking status for asthma research: evaluation of a natural language processing system" BMC Medical Informatics and Decision Making, vol. 6, Issue 30 (Jul. 2006), 9 pages.
Friedman et al. "Automated encoding of clinical documents based on natural language processing" Journal of the American Medical Informatics Association, vol. 11, Issue 5, (Sep./Oct. 2004), pp. 392-402.
Haug et al "Experience with a mixed semantic/syntactic parser" Proceedings of the Annual Symposium on Computer Applied Medical Care, (1995), pp. 284-288.
Taira et al. "A statistical natural language processor for medical reports" Proceedings of the AMIA Symposium, (1999), pp. 970-974.
Aronson "Effective mapping of biomedical text to the UMLS Metathesaurus: the MetaMap program", Proceedings of the AMIA Symposium, (2001), pp. 17-21.
Fiszman et al. "Automatic identification of pneumonia related concepts on chest x-ray reports" Proceedings of the AMIA Symposium, (1999), pp. 67-71.
Chapman et al. "A simple algorithm for identifying negated findings and diseases in discharge summaries" Journal of Biomedical Informatics, vol. 5, (2001), pp. 301-310.

* cited by examiner

EXTRACTION OF INFORMATION FROM CLINICAL REPORTS

BACKGROUND

With integrated information becoming available through large patient repositories, newer decision support systems are emerging that enable physicians to benefit from consensus opinions of other physicians who have looked at similar patients. These are based on techniques of content-based retrieval using underlying similarity in patients' diagnostic data to infer the similarity in their diagnosed diseases. An important source of diagnostic information is the measurement reports. These documents summarize the findings in many diagnostic settings and record important measurements taken from devices under various tests. Such reports also may contain written descriptions of the various structures and document concrete findings that point to diagnosis conclusions.

While complete natural language understanding of such reports is a challenging problem, often what needs to be extracted from these reports is sufficient clinical information to complete a longitudinal clinical record of the patient. Although electronic medical record systems capture clinical data, the information useful for diagnosis often lies in other systems and in unstructured form so that completing a full longitudinal record of a patient can require analysis of the unstructured data. The clinical reports, particularly those available in transcription systems, radiology systems, cardiology systems, form an important source of clinical data, such as demographic information (immunization, allergies), family history (relative who had a disease), diagnostic exam measurements (e.g. area of left ventricle), medications, procedures and other treatments and their outcomes. Extracting these types of information can be reduced to two basic types of operations—namely, finding textual phrases that are indicative of the type of clinical information being extracted, and finding name-value pairs indicating the pairing of measurements to their values.

An example includes inferring diagnosis labels from reports, which is an important preprocessing step for many evidence generation activities in healthcare. Knowing the diagnosis label helps classify the data and use it for straightforward lookup of patients with specific diseases. It also allows the grouping of patients with similar diseases for decision support and enables a consistency checking of recorded diagnosis in electronic medical record (EMR) systems. It can also have implications for quality control and revenue cycle management because missing or incorrect diagnosis codes can lead to lost revenue from inadequate billing as well as liabilities and quality of care issues due to missed diagnoses.

Inferring diagnosis labels from reports can be quite challenging since doctors rarely use the same phrase as the definition of a diagnosis code (ICD9). For example, a diagnosis code of mitral stenosis (394.0) may have to be inferred from a description in text such as 'There is evidence of a stenosis of the mitral valve in the patient.'

Although free text search engines can find exact matches to words in phrases in such reports, they cannot easily handle variations in the formation of the phrase such as above that still preserve the overall meaning. Finding textual phrases corresponding to a desired piece of information (such as a diagnosis label) requires (a) knowing the relevant vocabulary terms, (b) pre-cataloging possible variations in their appearance in medical text, (c) spotting reliable negations that imply the opposite in meaning, and (d) robust algorithms for finding matching phrases that tolerate the variations in usage of terms.

SUMMARY

Embodiments of a system are described. In one embodiment, the system is a phrase matching system. The system includes a training engine configured to: learn terms and term variants from a training corpus, wherein the terms and the term variants correspond to a specialized dictionary related to the training corpus; and generate a list of negative indicators found in the training corpus; and a matching engine configured to: perform a partial match of the terms and the term variants in a set of electronic documents to create initial match results; and perform a negation test using the negative indicators and a positive terms test using the terms and the term variants on the initial match results to remove matches from the initial match results that fail either the negation test or the positive terms test, resulting in final match results. Other embodiments of the system are also described.

Embodiments of a computer program product are also described. In one embodiment, the computer program product includes a computer readable storage device to store a computer readable program, wherein the computer readable program, when executed by a processor within a computer, causes the computer to perform operations for extracting information from electronic documents. The operations include: learning terms and term variants from a training corpus, wherein the terms and the term variants correspond to a specialized dictionary related to the training corpus; generating a list of negative indicators found in the training corpus; performing a partial match of the terms and the term variants in a set of electronic documents to create initial match results; and performing a negation test using the negative indicators and a positive terms test using the terms and the term variants on the initial match results to remove matches from the initial match results that fail either the negation test or the positive terms test, resulting in final match results. Other embodiments of the apparatus are also described.

Embodiments of a method are also described. In one embodiment, the method is a method for extracting information from electronic documents. The method includes: learning terms and term variants from a training corpus, wherein the terms and the term variants correspond to a specialized dictionary related to the training corpus; generating a list of negative indicators found in the training corpus; performing a partial match of the terms and the term variants in a set of electronic documents to create initial match results; and performing a negation test using the negative indicators and a positive terms test using the terms and the term variants on the initial match results to remove matches from the initial match results that fail either the negation test or the positive terms test, resulting in final match results. Other embodiments of the method are also described.

BRIEF DESCRIPTION OF THE DRAWINGS

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments present a system and method for extracting information from electronic documents based on terms and term variants corresponding to a given dictionary. More specifically, the system automatically learns a set of terms and variants of the terms from a training corpus of documents related to a dictionary before analyzing the electronic documents to be matched to the dictionary. In some embodiments, the learned terms and term variants may be manually curated to optimize the terms and term variants used when matching the electronic documents. The system performs a partial match on the electronic documents to narrow the set of documents. The system then performs a negation test and a positive terms test on the partial match results to obtain final match results by removing any partial matches that fail either test. In one embodiment, the system and method are used to extract diagnosis labels corresponding to International Statistical Classification of Diseases and Related Health Problems version 9 (ICD-9), or any version of the ICD, from textual clinical reports.

Some conventional systems extract principal diagnosis and co-morbidity from specific reports (e.g. asthma reports) using natural language processing systems in conjunction with other techniques, such as word stemming, sentence parsing techniques, dictionary-based approaches, stop-word removal, term spotting, negation finding, etc. While these systems may provide good precision matching, the recall of such systems may be low. Other conventional systems may provide good recall, but low precision matching. A system and method that performs an initial partial match based on a longest common subfix or subset of words using prefixes of the terms and term variants, where the terms and term variants are manually curated, provides for high precision and high recall.

Figure 1:
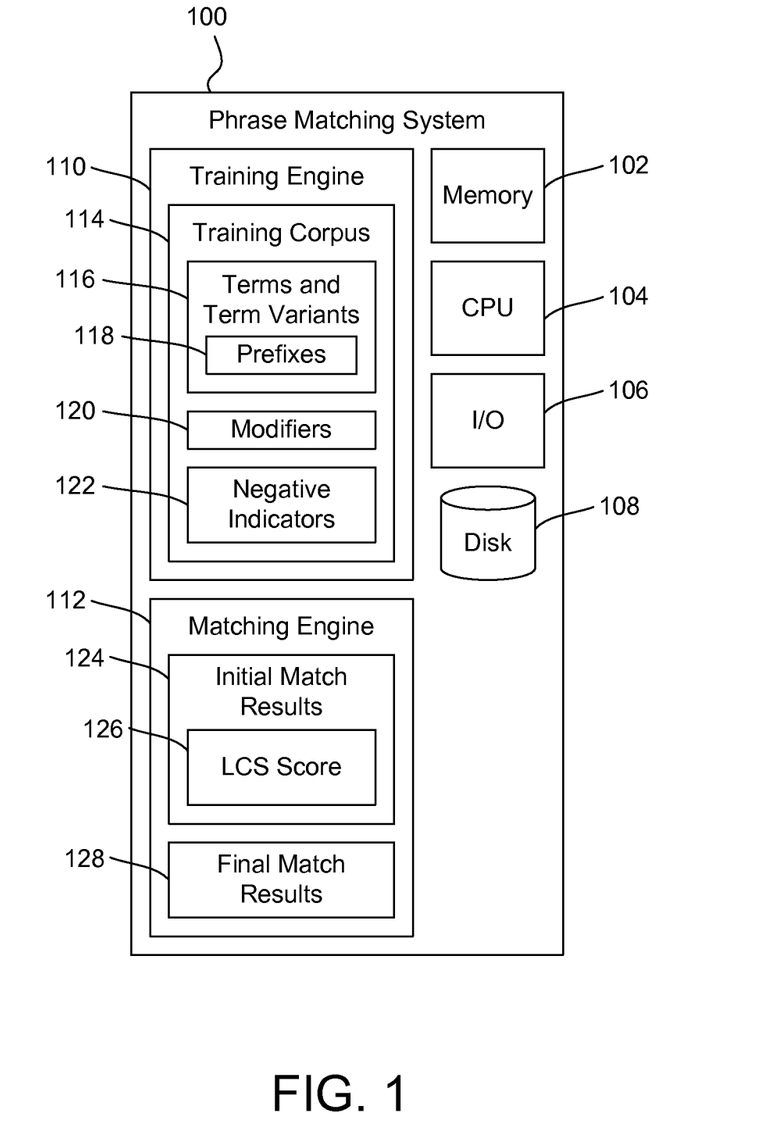
FIG. 1 depicts a schematic diagram of one embodiment of a phrase matching system.
Figure 4:
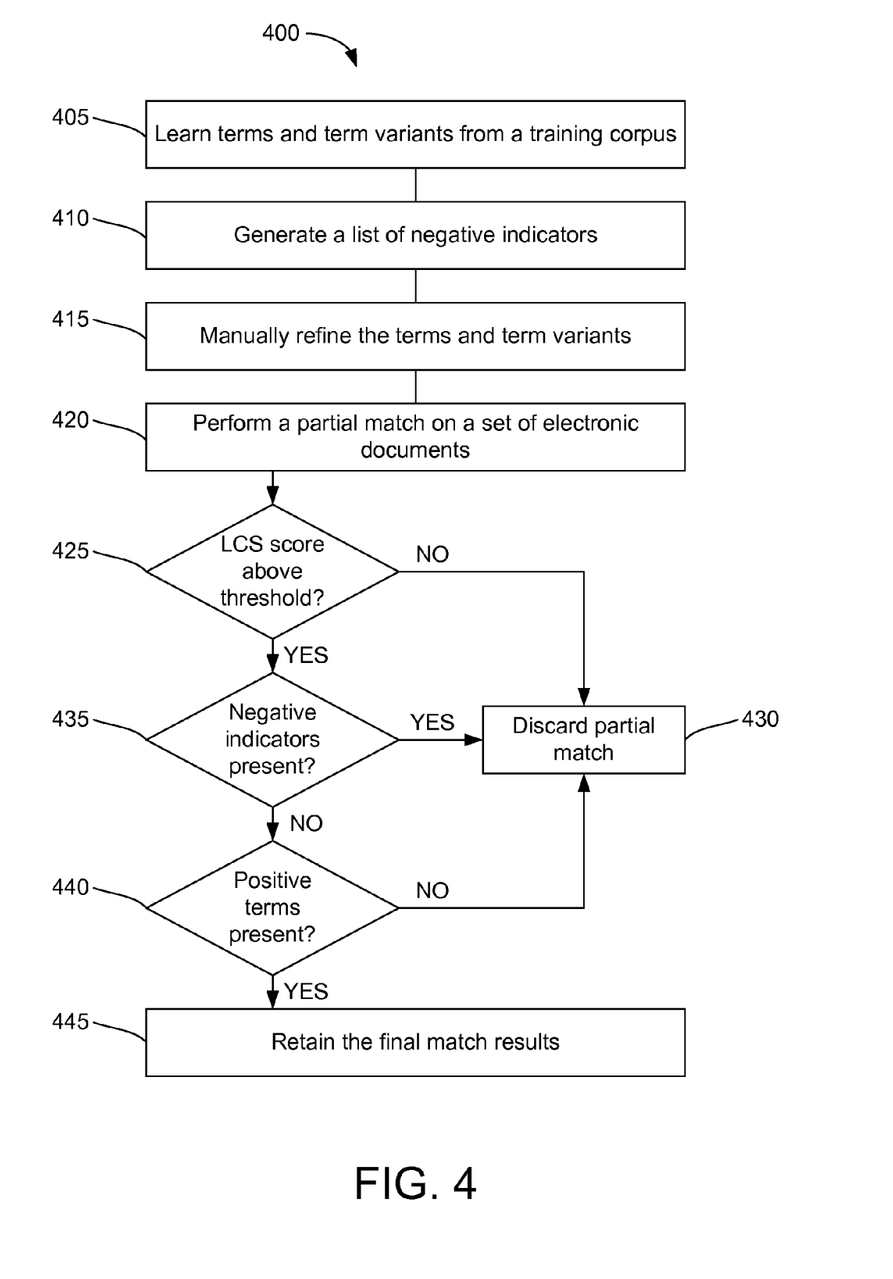
FIG. 4 depicts a flowchart diagram of one embodiment of a method for extracting information from electronic documents.

FIG. 1 depicts a schematic diagram of one embodiment of a phrase matching system 100. The depicted phrase matching system 100 includes various components, described in more detail below, that are capable of performing the functions and operations described herein. In one embodiment, at least some of the components of the phrase matching system 100 are implemented in a computer system. For example, the functionality of one or more components of the phrase matching system 100 may be implemented by computer program instructions stored on a computer memory device 102 and executed by a processing device 104 such as a CPU. The phrase matching system 100 may include other components, such as a disk storage drive 108, input/output devices 106, a training engine 110, and a matching engine 112. Some or all of the components of the phrase matching system 100 may be stored on a single computing device or on a network of computing devices, including a wireless communication network. The phrase matching system 100 may include more or fewer components or subsystems than those depicted herein. In some embodiments, the phrase matching system 100 may be used to implement the methods described herein as depicted in FIG. 4.

In one embodiment, the phrase matching system 100 includes a training engine 110. The training engine 110 allows the phrase matching system 100 to extract data from a training corpus 114 for a given application. The training corpus 114 may be related to a specialized dictionary that includes terms corresponding to the given application. The training corpus 114 may include a large number of electronic documents or reports known to include terms from the specialized dictionary. In one embodiment, the training engine 110 learns the terms and term variants 116 from the training corpus 114 based on data contained in the training corpus 114.

The term variants may include synonyms of the terms, words that share common stems with the terms, and other variants of the terms. In one embodiment, the term variants include a prefix 118 for each of the terms. The prefix 118 for each of a term may be a unique prefix 118 shared by only the term and variants of the term. In some embodiments, the unique prefix 118 may be a word stem shared by the term and the term variants. In some embodiments, the prefix 118 may be any length of prefix 118 for the terms and term variants 116 such that the prefix 118 is still unique.

In one embodiment, the training engine 110 is configured to learn modifiers 120 for the terms and term variants 116, including adjectives that describe a severity, amount, size, etc. of the terms and term variants 116 (such as "moderate," or "extreme") and other modifiers 120. In some embodiments, the training engine 110 may learn the modifiers 120 automatically via the training corpus 114. In other embodiments, the training engine 110 may learn the modifiers 120 via a manual input.

The training engine 110 may also learn negative indicators 122 included in the training corpus 114 in relation to the terms and term variants 116. Negative indicators 122 may include words or phrases of negation used within a predetermined proximity of the terms or term variants 116 to indicate an absence of a condition related to the terms or term variants 116. For example, if a phrase that includes the terms or term variants 116 otherwise indicates a presence of a certain medical or other condition, a negative indicator 122 in the phrase indicates that the condition is absent.

In one embodiment, the phrase matching system 100 includes a matching engine 112. The matching engine 112 may be configured to match the terms and term variants 116 to a set of electronic documents. Matches in the electronic documents may be displayed on a display device or other output device for a user to view. In one embodiment, the matching engine 112 obtains partial, initial match results 124 to narrow the material in the electronic documents. The initial match results 124 may be based on a longest common subfix (LCS) of words in a phrase containing one or more of the terms and term variants 116. In some embodiments, the set of electronic documents may not include the exact terms and term variants 116 to match a related condition or phrase in the specialized dictionary. Consequently, using the LCS to create the initial partial match results may allow the matching engine 112 to find matches that would have been missed by searching only for the exact phrase.

The LCS may be a subset of words in which each word is a prefix 118 of one of the terms or term variants 116 in the same order of their occurrence. In one embodiment, the prefix 118 for each of the terms and term variants 116 is a longest common prefix 118 shared by the words in the query phrase. For example, a query phrase attempting to match the terms "mitral valvular regurgitation" may match a subfix in a string such as, "Patient's mitral valve has shown evidence of regurgitating". In this example, the LCS between the query phrase and the given string or sentence is "mitral valv regurgitate". As described herein, the LCS may include prefixes 118 for each term or term variant common to words in the string being matched.

In one embodiment, the matching engine 112 is configured to determine an LCS score 126 for each parsed sentence or phrase in the electronic documents. The set of candidate phrases where the LCS has a score greater than a predetermined threshold may be retained as candidate matches in the initial match results 124. Each retained phrase may then be evaluated for negative and positive evidence of the query phrase in detail for final match results 128.

To look for negative indications, the matching engine 112 may examine a region around each subfix in the sentence for candidate negations, such as any negations learned by the training engine 110. The negations may be learned by examining common patterns of sentences or phrases occurring in the training corpus 114 and noting any negations included in the phrases. Each negation may be an ordered set of words giving negative indications of a condition. The region searched for negative indications around a subfix may be the smallest enclosing predicate in a sentence. Common conjunctions such as "and", "but" and "with" may be used to segment the sentence for such phrasal regions. Other enhancements to do phrasal extraction available in natural language processing (NLP) algorithms and methods may also be used for this task.

The matching engine 112 may also look for positive indications of phrases expected in the ICD-9 code label description. These terms may be required by the matching engine 112 to return a positive result, and may be pre-assembled from the ICD-9 code label descriptions during a prior training stage against a large training corpus 114 using the training engine 110. In some embodiments, general positive indication terms may be learned by the training engine 110 (e.g. "patient has . . . ").

The partial match results increase robustness of detection of the terms and term variants 116. In some embodiments, the partial match results based on the LCS may introduce some false positives, but this may be overcome by performing the negation and positive terms tests to lower the number of false positives as well as the number of false negatives.

Figure 2:
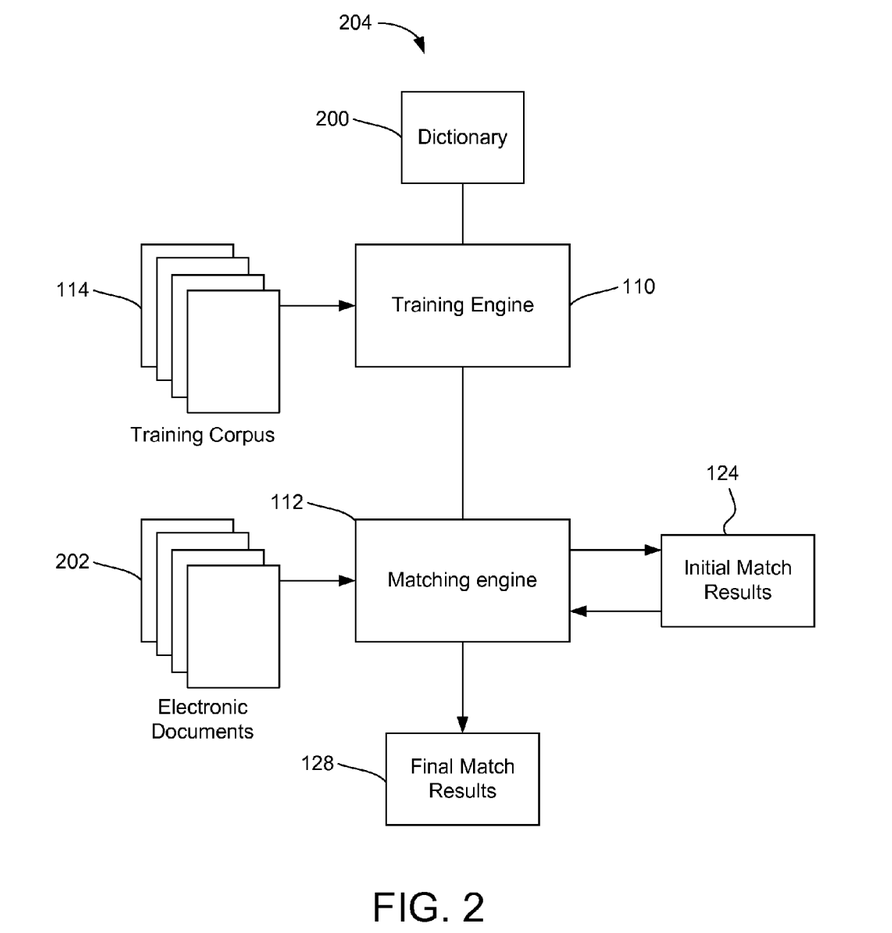
FIG. 2 depicts a flowchart diagram of one embodiment of a method for extracting information from electronic documents.

FIG. 2 depicts a flowchart diagram of one embodiment of a method 204 for extracting information from electronic documents. Although the method 204 is described in conjunction with the phrase matching system 100 of FIG. 1, embodiments of the method 204 may be implemented with other types of phrase matching systems 100.

In one embodiment, the training engine 110 receives a training corpus 114 of compiled documents. The training corpus 114 corresponds to a specialized dictionary 200 relating to each of the compiled documents. The specialized dictionary 200 may include words or phrases, such as medical terms or disease labels. In one embodiment, the set of documents in the training corpus 114 includes different iterations of a single report or document. In some embodiments, the training corpus 114 includes a variety of document types corresponding to the specialized dictionary 200.

The training engine 110 may extract the terms from the phrases/words in the training corpus 114 that correspond to the dictionary 200. In some embodiments, the training engine 110 then learns variants of each term by determining word roots for the terms and finding other words either in the training corpus 114 or a general dictionary 200 for words that share the word roots. In other embodiments, the training engine 110 may learn the term variants by determining synonyms of the terms. Other methods may be used to learn the term variants.

When the training engine 110 has learned the terms and term variants 116, the matching engine 112 uses the terms and term variants 116 to find matches in a set of electronic documents 202. The set of electronic documents 202 may be any set of electronic documents 202 capable of being searched, parsed and matched to the terms and term variants 116. In one embodiment, the matching engine 112 uses the terms and term variants 116 to find partial, initial match results 124 and retains documents with a certain percentage of the words in matching in the original order as described in the dictionary 200.

After obtaining the initial match results 124, the matching engine 112 then obtains the final match results 128 from the initial match results 124. In some embodiments, the matching engine 112 obtains the final match results 128 by performing negation and positive terms tests on the initial match results 124. The negation test may include searching for negative indicators 122 in the initial match results 124 and discarding any results that have negative indicators 122. The positive terms test may include searching for key words or phrases that are required to appear in the initial match results 124 and discarding any results that do not include the positive terms.

Figure 3:
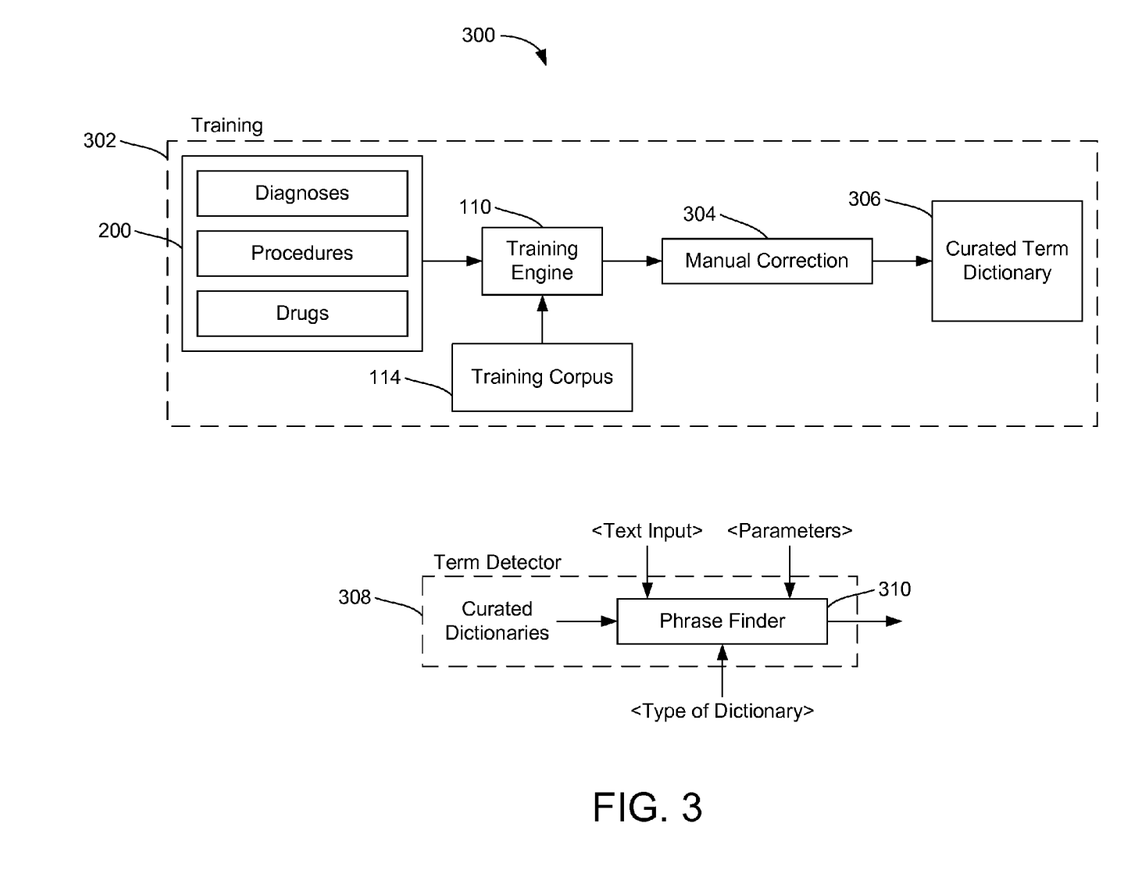
FIG. 3 depicts a flowchart diagram of one embodiment of a method for extracting information from electronic documents.

FIG. 3 depicts a flowchart diagram of one embodiment of a method 300 for extracting information from electronic documents. Although the method 300 is described in conjunction with the phrase matching system 100 of FIG. 1, embodiments of the method 300 may be implemented with other types of phrase matching systems 100.

In one embodiment, the phrase matching system 100 includes a training process 302 to create a curated term dictionary 306 corresponding to a specialized dictionary 200 of medical terms and phrases, such as an ICD-9 source dictionary. The dictionary 200 may include diagnoses, procedures, drugs, and other medical terminology. The training process 302 may include importing the dictionary 200 and a training corpus 114 related to the dictionary 200 into the training engine 110. The training engine 110 uses the terms and phrases in the dictionary 200 to learn the terms and variants of the terms used in the training corpus 114. The training engine 110 may extract all words from the training corpus 114 and parse them into sentences using language processing techniques. In some embodiments, the parsed sentences in the training corpus 114 may include negative indicators 122 or positive terms used in conjunction with the terms and term variants 116 from the dictionary 200. In some embodiments, the training engine 110 may determine prefixes 118 for the terms and term variants 116 and store the prefixes in a prefix dictionary. The training engine 110 may also receive input from a general dictionary to determine additional words, such as conjunctions, that may aid the training engine 110 in parsing and learning the terms and term variants 116.

In one embodiment, after the training engine 110 has learned the terms and term variants 116, negative indicators 122, and/or positive terms, the learned words and phrases may be manually curated 304 or corrected. For example, a physician with knowledge of the terms and term variants 116 in the dictionary 200 may manually filter the list of learned words and phrases by selecting key terms to be used by the matching engine 112 and removing other terms that are not necessary. The manually curated words and phrases may be stored in a curated term dictionary 306 to be used in conjunction with the matching engine 112.

In one embodiment, the matching engine 112 includes a term detector 308. The term detector may include a phrase finder 310 configured to parse phrases in a text input from a set of electronic documents 202 to be matched to the terms and term variants 116 in the curated term dictionary 306. In some embodiments, the term detector may include input from more than one curated term dictionary 306. The phrase finder 310 may receive search parameters that determine how to parse the text input and other aspects of the matching engine 112. In some embodiments, the term detector 310 may include an input to indicate the type of dictionary 306 that is being used to match against the text input. This may be especially useful in embodiments in which the term detector 308 may be used for multiple applications that use separate specialized or curated dictionaries 306. The phrase finder 310 may be configured to search the text input for sentences or phrases that include the terms and term variants 116 from the curated dictionaries 306 to produce match results.

FIG. 4 depicts a flowchart diagram of one embodiment of a method 400 for extracting information from electronic documents. Although the method 400 is described in conjunction with the phrase matching system 100 of FIG. 1, embodiments of the method 400 may be implemented with other types of phrase matching systems 100.

In one embodiment, the phrase matching system 100 learns 405 terms and term variants 116 from a training corpus 114. The terms and term variants 116 may correspond to a specialized dictionary 200, such as an ICD-9 source dictionary that includes disease label code names. In some embodiments, the ICD-9 source dictionary may be partitioned into smaller dictionaries by disease category or some other subset of the dictionary 200.

The phrase matching system 100 may then generate 410 a list of negative indicators 122 found in the training corpus 114. In one embodiment, the phrase matching system 100 generates the list of negative indicators 122 using an N-gram parameter that determines a maximum number of consecutive words for each phrase in which the negative indicators 122 are found. A phrase in which a negative indicator 122 is found may be a part or all of any given sentence.

In one embodiment, the phrase matching system 100 receives an input to manually refine 415 the terms and term variants 116 learned from the training corpus 114 before performing the partial match. The manual refinement may include removing terms or term variants 116 or adding additional terms or term variants 116. The manual refinement may also include modifying the negative indicators 122 and positive terms used by the phrase matching system 100 to obtain the final match results 128.

In one embodiment the phrase matching system 100 performs 420 a partial match of the terms and term variants 116 on a set of electronic documents 202 to create initial match results 124. In one embodiment, performing the partial prefix match includes segmenting the set of electronic documents 202 into sentences. After segmenting the set of electronic documents 202, the phrase matching system 100 may determine 425 an LCS score 126 for each sentence when performing the partial match. The LCS score 126 may correspond to a maximum subset of term and term variant matches for each sentences. Sentences with an LCS score 126 above a predetermined threshold may be retained. If the LCS score 126 is below the threshold, the partial match is discarded 430.

In one embodiment, the phrase matching system 100 performs 435 a negation test on the initial match results 124 using the negative indicators 122 learned from the training corpus 114. In one embodiment, the phrase matching system 100 also performs 440 a positive terms test using the terms and term variants 116 on the initial match results 124. In one embodiment, the positive terms test includes searching for term modifiers 120, which modify the terms and term variants 116, within the maximum number of words according to the N-gram parameter. Term modifiers 120 may include adjectives that describe a severity of a condition ("moderate," "severe," etc.).

The phrase matching system 100 may then discard 430 partial matches from the initial results that fail either the negation test or the positive terms test. The partial matches that pass the negation test and the positive terms test are retained 445 for final match results 128.

In one embodiment, learning the terms and term variants 116 includes learning a common prefix 118 for each term and term variant. The common prefix 118 may be unique to a single word. The prefixes 118 may be a word stem, in some embodiments. In some embodiments, the common prefix 118 may be any length to satisfy a uniqueness requirement. In one embodiment, performing a partial match includes matching the common prefix 118 for each term and term variant to the set of electronic documents 202. Matching the common prefix 118 for each term may allow the phrase matching system 100 to quickly determine whether a specific term is located in each target sentence or phrase. For example, if the term to be searched starts with an "m" and the target sentence does not include any words that begin with the letter "m", the phrase matching system 100 knows that the term is not included in the target sentence.

One embodiment of an algorithm used by the phrase matching system 100 is described below. The phrase matching system 100 may learn a list of diagnosis phrases pointing to ICD codes taking into account the name variants for common medical terms (e.g. regurgitation and insufficiency are synonyms) and a set of minimum prefixes 118 needed for a positive identification of these phrases to form a specialized ICD-9 dictionary. Sentences are then extracted from text reports using any of the standard sentence separation techniques in literature. A set of partial match terms is found in each sentence using a new algorithm that finds the longest common subfix in a phrase. Each such retained sentence is then evaluated for negative and positive evidence of the query phrase in detail. Finally, the algorithm looks for positive indications of phrases expected in the ICD-9 code label description.

In one embodiment, the algorithm first automatically analyzes an ICD-9 code dictionary with key terms that is also physician curated.

1. Extract all words from a large training corpus of actual reports, and create an inverted dictionary of all non-stop words and all their prefixes. If a prefix is shared by more than one word a Boolean flag is placed. This forms the prefix dictionary.
2. Starting from a list of ICD-9 disease label code names, each non-stop word in the name phrase is looked up in the prefix dictionary and its largest prefix that is unique (Boolean flag is false) is retained. In some cases, the entire word may be retained.
3. From the collected list of candidate prefixes retain key terms (manually curated by physicians). The prefixes may ensure that the smallest substrings for indication of the disease label phrase are retained to maximize the recall. The final filtering by physicians may ensure that the prefixes retained are of clinically significant terms. For example, one common word found in the ICD-9 disease labels is "unspecified". In the prefix form, the term formed from this may be "unspecif". Because this is rarely mentioned in the actual description of the disease and may have to be inferred, the physician may decide to leave this out as a search term.

The algorithm then discovers a list of negation terms by mining a large collection of reports. Some negative indicators 122, such as "no" and "not found" may be noted easily. For more obscure negative indicators 122, a constrained, iterative combination generation process based on frequency of occurrence of sub-phrases may be used. Negative indicators 122 may include a relatively small number of words in phrases. Given a large training corpus 114, all N-grams from each sentence may be extracted from the corpus as follows:

1. Segment reports into sentences. Different sentence extraction techniques may be used for this purpose.
2. Group K consecutive words into phrases (including stop words) where K is varied. Different ranges of K may be tried, though a range of 1 to 10 may be used based on the assumption that fragments of negation N-grams can be found in one of these consecutive word groups called phraselets.
3. Plot the frequency of occurrence of these phraselets across the collection in ranked order, and retain M choices manually based on their partial evidence for negations. For example, the phrase "there is no evidence of..." may be a clear choice. Automatic screening may give an observer the range of possible phrases from which to select. In one embodiment, physician knowledge of reports is applied to do the M selections.
4. From the retained phrases, M phrases form M×M/2 combinations of phrases for expanding the search of negations. For example, phrase "there is no evidence of..." and "...but was not seen" may be joined into one phrase—"there is no evidence of <tab> but was not seen".
5. Each retained phrase may then be searched throughout all sentences in the training corpus using a partial match algorithm of longest common prefix with a prefix cutoff score of 1.0—each word in the phrase has an exact match if present. The frequency of occurrence of each such phrase may be noted. The "<tab>" in the joined phrase may be ignored during phrasal matching.
6. Repeat operations 3-5 with newly obtained phraselets until the frequency of occurrence of the highest term drops to a predetermined threshold (for example, <1%) or the number of words in the phrase exceeds a maximum number.
7. The list of final phraselets retained form the negation N-grams. Each consecutive word block in the N-gram is separated by "<tab>" to allow for both exact matches (for the consecutive word block) and partial matches (between the words separated by "tab").

Operations for learning the terms and term variants 116 and the negative indicators 122 may be performed in polynomial time to avoid exponential subset operations that may be needed otherwise. Additionally, such operations may be performed prior to matching any documents.

The algorithm then performs a partial match algorithm based on the longest common subfix. Given the list of disease names from the curated ICD-9 dictionary, and a new report from which the diagnosis codes are to be inferred, the algorithm runs as follows:

1. Segment the report into sentences.
2. For all disease names from the curated ICD-9 dictionary, a partial match with the sentences is performed. Those that have a score of longest common subfix (LCSx) above a threshold are retained. A different choice of threshold varies precision and recall and can be chosen based on the desired precision and recall from the Receiver Operating Characteristic (ROC) curve. In one embodiment, a choice of 0.6 is used. The longest common subfix is found using dynamic programming as follows:
    a. Given a query phrase $S=\{s1,s2,...sK\}$ K words and a candidate sentence $T=\{t1,t2,....tN\}$, then the longest common subfix $LCSx(S,T)=\{c1,c2...cL\}$ where L is the largest subset of words from S that found a partial match in T. A partial match of a word $si$ in S is a word $tj$ in T with a shared prefix greater than a threshold. Making the threshold 1.0 reduces to the case of finding exact matches to words of S, even though the longest common subsequence still allows a partial number of words in S to match. The longest common subfix may be found using dynamic programming similar to a longest common subsequence but with the important modification to do dynamic programming at the word level and using prefix matches. For this, an array $C[i,j]$ is used to calculate the score of matching a fragment of S up to the ith word and fragment of T up to the jth word as follows:

```
LCSx(S,T):
C[i,0]=0 for all 0<=i<=K
C[0,j]=0 for all 0<=j<=N.
for (1<=i<=K)
{
for (1<=j<=N)
   {
   prefix_score(i,j)=|longestprefix(si,tj)|/|si|
   if ((c[i-1][j-1]+prefix_score(i,j)>c[i-1][j]) &&
       (c[i-1][j-1]+prefix-score(i,j)>c[i][j-1]))
      {
           c[i][j]=c[i-1][j-1]+prefix_score(i,j);
      }
   else
      {
        if (c[i-1][j]>c[i][j-1])
           {
              c[i][j]=c[i-1][j];
           }
        else c[i][j]=c[i][j-1];
      }
   }
}
```

The algorithm also uses negation with positive indication terms during phrasal matches. Once the set of sentences that pass the partial phrase match are retained, further evidence of a diagnosis code inside the report is obtained as follows:

3. For each negation phraselet from the learned negation phraselist and a candidate partial match sentence:
   a. for each word group in a chosen phraselet
      i. if an exact match is not found for the word group, accept the partial match for the ICD code and quit.
   b. Abandon the partial match of ICD code if all word groups in the chosen phraselet match.
4. For each retained candidate partial match sentence, and the ICD-9 code disease label under consideration:
   a. for each must-have key term from the ICD-9 dictionary corresponding to the candidate disease label
      i. if an exact match to the key term is not found in the candidate sentence, abandon the match.
5. Retain all matching sentences and their corresponding ICD-9 codes and disease labels.
6. Remove duplicate ICD-9 codes and disease labels (different disease labels could have the same ICD-9 codes) for redundancy. This is the final list of inferred diagnosis labels from the report.

An embodiment of a phrase matching system 100 includes at least one processor coupled directly or indirectly to memory elements through a system bus such as a data, address, and/or control bus. The memory elements can include local memory employed during actual execution of the program code, bulk storage, and cache memories which provide temporary storage of at least some program code in order to reduce the number of times code must be retrieved from bulk storage during execution.

It should also be noted that at least some of the operations for the methods may be implemented using software instructions stored on a computer useable storage medium for execution by a computer. As an example, an embodiment of a computer program product includes a computer useable storage medium to store a computer readable program that, when executed on a computer, causes the computer to perform operations, including an operation to extract information from electronic documents.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Embodiments of the invention can take the form of an entirely hardware embodiment, an entirely software embodiment, or an embodiment containing both hardware and software elements. In one embodiment, the invention is implemented in software, which includes but is not limited to firmware, resident software, microcode, etc.

Furthermore, embodiments of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The computer-useable or computer-readable medium can be an electronic, magnetic, optical, electromagnetic, infrared, or semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Input/output or I/O devices (including but not limited to keyboards, displays, pointing devices, etc.) can be coupled to the system either directly or through intervening I/O controllers. Additionally, network adapters also may be coupled to the system to enable the data processing system to become coupled to other data processing systems or remote printers or storage devices through intervening private or public networks. Modems, cable modems, and Ethernet cards are just a few of the currently available types of network adapters.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:
1. A computer program product, comprising:
   a computer readable storage medium to store a computer readable program, wherein the computer readable program, when executed by a processor within a computer, causes the computer to perform operations for extracting information from electronic documents, the operations comprising:
      learning terms and term variants from a training corpus, wherein the terms and the term variants correspond to a specialized dictionary related to the training corpus;
      generating a list of negative indicators found in the training corpus;

performing a partial match of the terms and the term variants in a set of electronic documents to create initial match results; and performing a negation test using the negative indicators and a positive terms test using the terms and the term variants on the initial match results to remove matches from the initial match results that fail either the negation test or the positive terms test, resulting in final match results.

2. The computer program product of claim 1, wherein generating the list of negative indicators further comprises:

searching for the negative indicators in the training corpus using an N-gram parameter, wherein the N-gram parameter determines a maximum number of consecutive words for each phrase in which the negative indicators are found.

3. The computer program product of claim 2, wherein performing the positive terms test further comprises:

searching for term modifiers within the maximum number of words according to the N-gram parameter, wherein the term modifiers modify the terms and the term variants.

4. The computer program product of claim 1, wherein learning the terms and term variants further comprises learning a common prefix for each term and term variant, wherein each common prefix is unique to a single word.

5. The computer program product of claim 4, wherein performing the partial match further comprises matching the common prefix for each term and term variant to the set of electronic documents.

6. The computer program product of claim 1, wherein performing the partial prefix match further comprises:

segmenting the set of electronic documents into sentences;
determining a longest common subfix score for each sentence, wherein the longest common subfix score corresponds to a maximum subset of term and term variant matches for each sentence; and
retaining sentences that have the longest common subfix score above a predetermined threshold.

7. The computer program product of claim 1, wherein the computer readable program, when executed on the computer, causes the computer to perform additional operations, comprising:

manually refining the terms and the term variants learned from the training corpus before performing the partial match, wherein electronic documents comprise clinical reports.

8. A phrase matching system, comprising:

a training engine configured to:

learn terms and term variants from a training corpus, wherein the terms and the term variants correspond to a specialized dictionary related to the training corpus; and generate a list of negative indicators found in the training corpus; and a matching engine configured to:

perform a partial match of the terms and the term variants in a set of electronic documents to create initial match results; and perform a negation test using the negative indicators and a positive terms test using the terms and the term variants on the initial match results to remove matches from the initial match results that fail either the negation test or the positive terms test, resulting in final match results.

9. The system of claim 8, wherein generating the negative indicators further comprises:

searching for the negative indicators in the training corpus using an N-gram parameter, wherein the N-gram parameter determines a maximum number of consecutive words for each phrase in which the negative indicators are found.

10. The system of claim 9, wherein performing the positive terms test further comprises:

searching for term modifiers within the maximum number of words according to the N-gram parameter, wherein the term modifiers modify the terms and the term variants.

11. The system of claim 8, wherein learning the terms and term variants further comprises learning a common prefix for each term and term variant, wherein each common prefix is unique to a single word.

12. The system of claim 8, wherein performing the partial prefix match further comprises:

segmenting the set of electronic documents into sentences;
determining a longest common subfix score for each sentence, wherein the longest common subfix score corresponds to a maximum subset of term and term variant matches for each sentence; and
retaining sentences that have the longest common subfix score above a predetermined threshold.

13. The system of claim 8, wherein the training engine is further configured to:

receive an input to manually refine the terms and the term variants learned from the training corpus, wherein electronic documents comprise clinical reports.

\* \* \* \* \*